(12) United States Patent
Park et al.

(10) Patent No.: US 9,782,062 B2
(45) Date of Patent: Oct. 10, 2017

(54) LOCALLY INVASIVE SURGICAL APPARATUS WITH MANIPULATOR FOR BONE FRACTURE TREATMENT

(71) Applicant: Kyungpook National University Industry—Academic Cooperation Foundation, Daegu (KR)

(72) Inventors: Il Hyung Park, Daegu (KR); Chul Woo Park, Daegu (KR); Sang Hyun Joung, Daegu (KR)

(73) Assignee: Kyungpook National University Industry-Academic Cooperation Foundation, Daegu (KR)

( * ) Notice: Subject to any disclaimer, the term of this patent is extended or adjusted under 35 U.S.C. 154(b) by 89 days.

(21) Appl. No.: 14/773,225

(22) PCT Filed: Mar. 4, 2014

(86) PCT No.: PCT/KR2014/001767
§ 371 (c)(1),
(2) Date: Sep. 4, 2015

(87) PCT Pub. No.: WO2014/157845
PCT Pub. Date: Oct. 2, 2014

(65) Prior Publication Data
US 2016/0015460 A1    Jan. 21, 2016

(30) Foreign Application Priority Data
Mar. 26, 2013 (KR) .......................... 10-2013-0032198

(51) Int. Cl.
*A61B 1/317* (2006.01)
*A61B 1/00* (2006.01)
(Continued)

(52) U.S. Cl.
CPC ............ *A61B 1/317* (2013.01); *A61B 1/0016* (2013.01); *A61B 1/0055* (2013.01);
(Continued)

(58) Field of Classification Search
CPC .............. A61B 1/317; A61B 2034/301; A61B 2034/302; A61B 2034/303;
(Continued)

(56) References Cited

U.S. PATENT DOCUMENTS 5,546,942 A     8/1996  Zhang
5,667,473 A *   9/1997  Finn .................... A61B 1/00165
                                                            385/117
(Continued)

FOREIGN PATENT DOCUMENTS

JP      2001-511043 A     8/2001
KR     10-2009-0005316 A  1/2009

*Primary Examiner* — Ryan Henderson
(74) *Attorney, Agent, or Firm* — Novick, Kim & Lee, PLLC; Sang Ho Lee

(57) ABSTRACT

The present invention provides a locally invasive surgical apparatus including a manipulator for scratching the bone at a fracture site, a drive arm on which the manipulator is mounted, and a controller for controlling the manipulator and the drive arm. Therefore, it is possible to carry out minimally invasive surgery during bone fracture surgery, thereby enabling simple and quick bone fracture surgery for a speedy recovery.

12 Claims, 6 Drawing Sheets

(51) Int. Cl.

| | | |
|---|---|---|
| *A61B 1/005* | (2006.01) | |
| *A61B 17/16* | (2006.01) | |
| *A61B 17/72* | (2006.01) | |
| *A61B 1/06* | (2006.01) | |
| *A61B 17/32* | (2006.01) | |
| *A61B 34/30* | (2016.01) | |
| *A61B 34/37* | (2016.01) | |
| *A61B 34/00* | (2016.01) | |
| *A61B 90/30* | (2016.01) | |

(52) U.S. Cl.
CPC ...... *A61B 1/00087* (2013.01); *A61B 1/00147* (2013.01); *A61B 1/00149* (2013.01); *A61B 1/0684* (2013.01); *A61B 17/1659* (2013.01); *A61B 17/320016* (2013.01); *A61B 17/72* (2013.01); *A61B 34/30* (2016.02); *A61B 34/37* (2016.02); *A61B 34/72* (2016.02); *A61B 2090/309* (2016.02)

(58) Field of Classification Search
CPC ........ A61B 2034/304; A61B 2034/305; A61B 2034/306; A61B 34/30; A61B 34/35; A61B 34/37; A61B 1/00131; A61B 1/00133; A61B 1/00147; A61B 1/00149; A61B 1/016; A61B 1/0055; A61B 1/008; A61B 1/01; A61B 1/06; A61B 1/0615; A61B 1/0623; A61B 1/0661; A61B 1/0676; A61B 1/0684; A61B 1/313; A61B 1/3132; A61B 1/3135; A61B 1/3137; A61B 1/32; A61B 17/1659; A61B 17/1735; A61B 17/320016; A61B 2017/320028; A61B 2017/32004
USPC ........ 600/104, 106, 107, 114–118, 427, 429; 606/1, 130
See application file for complete search history.

(56) References Cited

U.S. PATENT DOCUMENTS

| | | | |
|---|---|---|---|
| 6,837,892 | B2 | 1/2005 | Shoham |
| 8,328,808 | B2 | 12/2012 | Guzman et al. |
| 2005/0096502 | A1 | 5/2005 | Khalili |
| 2007/0016174 | A1 | 1/2007 | Millman et al. |
| 2010/0292749 | A1* | 11/2010 | Stewart .............. A61B 18/1445 607/9 |
| 2012/0053597 | A1 | 3/2012 | Anvari et al. |
| 2013/0096574 | A1* | 4/2013 | Kang ................. A61B 17/1622 606/130 |
| 2013/0345717 | A1* | 12/2013 | Markvicka ............ A61B 34/30 606/130 |

* cited by examiner

LOCALLY INVASIVE SURGICAL APPARATUS WITH MANIPULATOR FOR BONE FRACTURE TREATMENT

TECHNICAL FIELD

The present invention relates to a locally invasive surgical apparatus including a manipulator for bone fracture treatment, and more particularly, to a locally invasive surgical apparatus including a manipulator for bone fracture treatment, in which the manipulator minimally invades a fracture area of delayed conglutination and non-conglutination.

BACKGROUND ART

A fracture indicates a state in which a bone is partially or completely broken due to an external force. The fracture may occur in a bone inside a body, for example, the femur or the ulna and additionally a flat bone and cranial bones.

A surgery is performed on a fracture area described above as follows.

FIG. 1 is a view illustrating a state in which a bone (femur) 1 on which a fracture surgery is performed is delay-conglutinated and not conglutinated.

Referring to FIG. 1, in treatment for fracture, a fracture end is adhered to a regular position thereof and immovably fixed until synostosis of both sides is recovered.

When a fracture occurs in an area of a long bone to which a strong muscle is attached, it is not easy to adhere and fix fractured bones to each other. Accordingly, various methods have been conceived and studied for a long time.

Put simply, even when a splint is attached and externally fixes them, the fractured end is generally twisted. Also, it is impossible to expect complete fixing. Accordingly, during the surgery, as shown in the drawing, a method in which a shaft 10 made of a metal material is put thereon and fixed thereto using screws 20 is generally used.

However, cases in which a synostosis stops progressing and a false joint is formed, non-conglutination maintains in a state in which fibrous conglutination is formed, or conglutination is progressing but consumes a longer time than a normal conglutination time occur in about 10% of patients after fracture surgery.

In this case, in a typical treatment for delayed conglutination and non-conglutination, flesh of a fracture area which has a problem is largely cut to expose a bone and the exposed bone is intentionally wounded to induce forming a callus.

However, since the surgery is performed while the bone of the fracture area of delayed conglutination and non-conglutination is completely exposed in the treatment described above, an incision necessary for the surgery is large and thus a surgical time would be increased and bleeding of a patient would be increased as well.

Also, since the surgery is performed while the bone of the fracture area is completely exposed, the recovery is slow.

DISCLOSURE

Technical Problem

An aspect of the present invention is to provide an apparatus capable of performing minimally invasive surgery for scratching a fracture area to form a callus for delayed conglutination and non-conglutination.

Another aspect of the present invention is to provide an apparatus capable of performing fracture surgery which is simple and quick and allows quick recovery.

Technical Solution

One aspect of the present invention provides a locally invasive surgical apparatus including a manipulator for fracture treatment. The apparatus includes the manipulator for scratching a bone of a fracture area, a driving arm on which the manipulator is mounted, and a controller for controlling the manipulator and the driving arm.

The manipulator may include a surgical space providing unit which provides a surgical space by spacing the bone of the fracture area apart from soft tissue and a scratch forming unit for scratching the bone of the fracture area.

The manipulator may further include an endoscope for observing the fracture area. Herein, the apparatus may further include a display unit which displays a part observed by the endoscope.

The endoscope may be one of a two-dimensional (2D) endoscope and a three-dimensional (3D) endoscope.

The endoscope may be provided at one of the surgical space providing unit and the scratch forming unit.

The surgical space providing unit may include a supporting portion formed of a plurality of supporting pieces which are link-connected and bent and space and support the soft tissue apart from the bone and a peeling knife provided at a free end of the supporting portion to separate the bone and the soft tissue which are attached to each other.

The peeling knife may be formed to allow an end thereof to slant toward one side.

A link connecting portion of each of the supporting pieces may include an actuator to control a bending angle.

The surgical space providing unit may include a supporting hose which includes a hollow portion through which a gas or fluid flows therein and an outlet formed at one side to be connected to the hollow portion and to discharge the gas or fluid which flows therein and a supporting tube which is provided at an outer circumferential surface of the supporting hose while accommodating the outlet of the supporting hose and is filled with the gas or fluid discharged from the outlet to increase in volume, thereby spacing the soft tissue apart from the bone and supporting the spaced soft tissue.

The surgical space providing unit may further include at least one flat light emitting device at a bottom of the supporting portion.

The flat light emitting device may be a light emitting diode (LED).

The scratch forming unit may include a driving portion in which a plurality of driving pieces are link-connected and repeatedly move based on one link connecting portion to scratch the bone and a scratching blade provided at a free end of the driving portion to scratch a fracture area of the bone to form a callus.

The link connecting portion of the driving pieces may include an actuator to control a bending angle.

The scratch forming unit may further include at least one flat light emitting device at a bottom of the driving portion.

The flat light emitting device may be a light emitting diode (LED).

Advantageous Effects

The present invention provides an effect of performing minimally invasive fracture surgery which is simple and quick and allows quick recovery.

MODE FOR INVENTION

Figure 1:
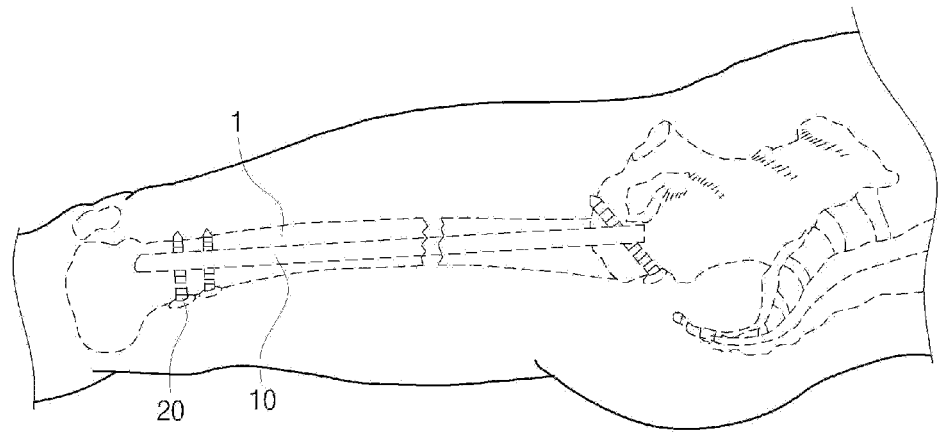
FIG. 1 is a view illustrating a state in which a bone (e.g., femur) on which a fracture surgery is performed is delay-conglutinated and not conglutinated.

Hereinafter, exemplary embodiments of the present invention will be described in detail with reference to the attached drawings.

Throughout the specification, unless otherwise defined, all terms are identical to a general meaning of terms understood by one of ordinary skill in the art. A term which conflicts with a general meaning thereof will be understood according to a meaning defined herein.

Put simply, the embodiments which will be described below are not intended as limitations and should be considered in a descriptive sense only. Throughout the specification, like reference numerals designate like elements.

Since the present invention has significant features in a surgical apparatus which enables minimally invasive surgery when revision surgery is performed to form a callus in cases of delayed conglutination and non-conglutination after fracture surgery, the particular features will be described below in detail with reference to the drawings.

Figure 2:
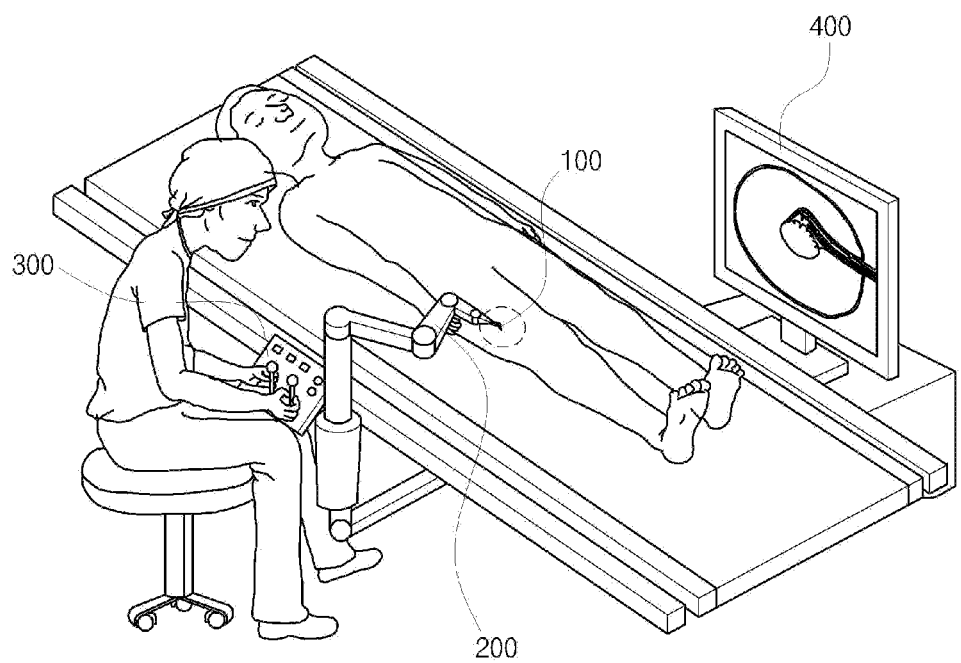
FIG. 2 is a schematic view illustrating a state of using a locally invasive surgical apparatus including a manipulator for fracture treatment according to one embodiment of the present invention.
Figure 3:
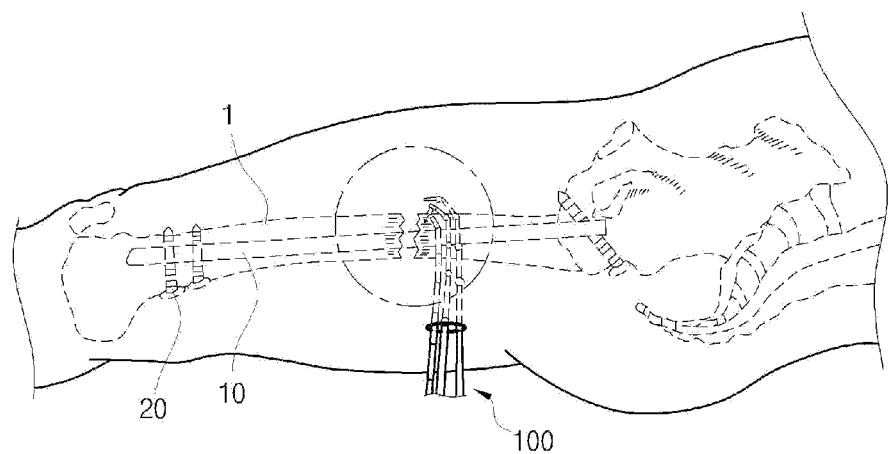
FIG. 3 is a schematic view illustrating a state in which the manipulator for fracture treatment performs surgery on a fracture area of a bone (femur) according to one embodiment of the present invention.
Figure 4:
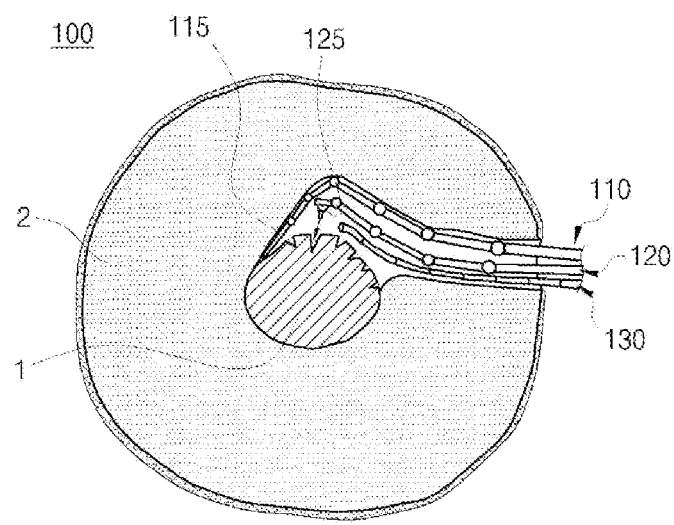
FIG. 4 is a cross-sectional view of the surgical state taken from FIG. 3.
Figure 5:
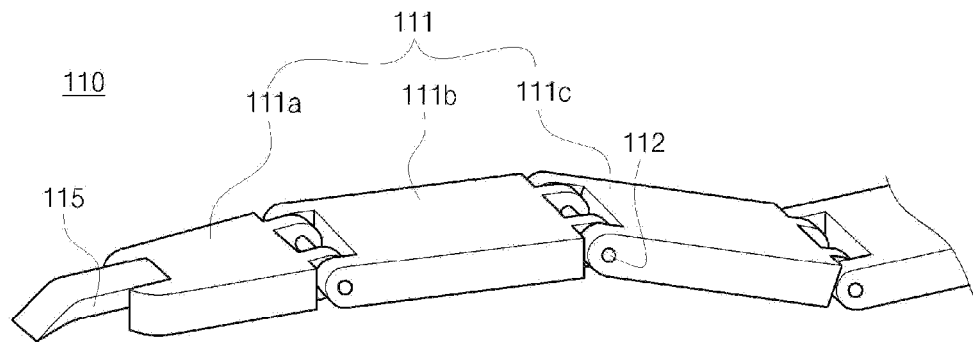
FIG. 5 is a front perspective view of a surgical space providing unit according to one embodiment of the present invention.
Figure 6:
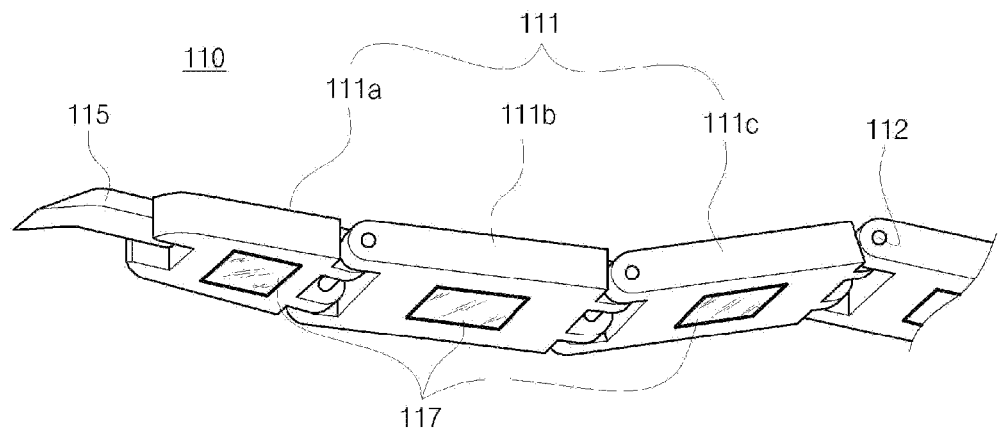
FIG. 6 is a rear perspective view of the surgical space providing unit including a flat light emitting device according to one embodiment of the present invention.
Figure 7:
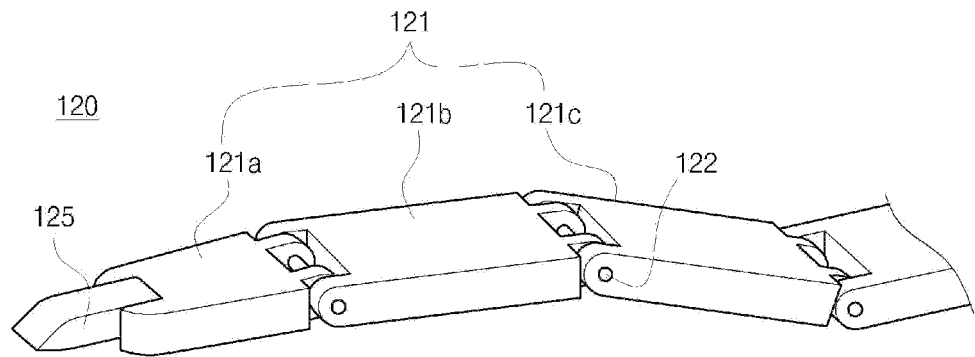
FIG. 7 is a perspective view of a scratch forming unit according to one embodiment of the present invention.
Figure 8:
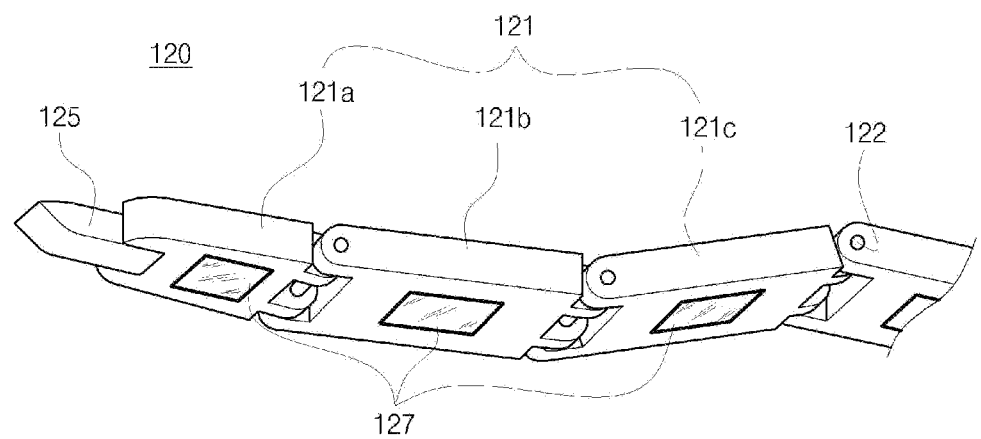
FIG. 8 is a rear view of the scratch forming unit including a flat light emitting device according to one embodiment of the present invention.

FIG. 2 is a schematic view illustrating a state of using a locally invasive surgical apparatus including a manipulator 100 for fracture treatment according to one embodiment of the present invention. FIG. 3 is a schematic view illustrating a state in which the manipulator 100 for fracture treatment performs surgery on a fracture area of a bone (femur) 1 according to one embodiment of the present invention. FIG. 4 is a cross-sectional view of the surgery state taken from FIG. 3. FIG. 5 is a perspective view of a surgical space providing unit according to one embodiment of the present invention. FIG. 6 is a rear view of the surgical space providing unit including a flat light emitting device according to one embodiment of the present invention. FIG. 7 is a perspective view of a scratch forming unit according to one embodiment of the present invention. FIG. 8 is a rear view of the scratch forming unit including a flat light emitting device according to one embodiment of the present invention.

Referring to FIG. 2, the locally invasive surgical apparatus for fracture treatment according to one embodiment includes the manipulator 100 for scratching the fracture area of a bone 1, a driving arm 200 on which the manipulator 100 is mounted, and a controller 300 for controlling the manipulator 100 and the driving arm 200.

Also, the locally invasive surgical apparatus for fracture treatment according to one embodiment of the present invention may further include a display unit 400 which displays an image of a part observed by an endoscope 130 which will be described below. A user may observe a surgical area in detail through the display unit 400 and may precisely control the manipulator 100 and the driving arm 200 by controlling the controller 300.

Meanwhile, referring to FIGS. 3 to 8, the manipulator 100 for fracture treatment according to one embodiment of the present invention includes a surgical space providing unit 110 which provides a surgical space by spacing the bone 1 apart from soft tissue 2 of the fracture area, a scratch forming unit 120 for scratching the fracture area of the bone 1, and the endoscope 130 for observing the fracture area.

The endoscope 130 may be provided as one of a two-dimensional (2D) endoscope and a three-dimensional (3D) endoscope. According to a purpose of surgery, the 2D endoscope or the 3D endoscope may be mounted in the manipulator 100.

The endoscope 130 may display a treatment area in a 2D image or a 3D image on the display unit 400 described above, thereby providing a more detailed image to the user who operates the driving arm 200 and the manipulator 100.

Meanwhile, the surgical space providing unit 110 includes a supporting portion 111 formed of a plurality of supporting pieces 111a, 111b, and 111c linked with and bent to space and support the soft tissue 2 and a peeling knife 115 provided at a free end of the supporting portion 111 to separate the bone 1 from the soft tissue 2 which are attached to each other.

The peeling knife 115 separates the bone 1 from the soft tissue 2 when the surgical space providing unit 110 is inserted into an invasive area. Accordingly, to efficiently separate the soft tissue 2, a width of the peeling knife 115 may be wider than a scratching blade 125 which will be described below and a blade end thereof may slant toward one side. A slant direction of the peeling knife 115 faces the bone 1 to more easily separate the bone 1 from the soft tissue 2.

To allow the scratch forming unit 120 to perform an operation, the supporting portion 111 supports the soft tissue 2 while spacing the soft tissue 2 separated from the bone 1 by the peeling knife 115 apart from the bone 1. Also, a link connecting portion 112 of each of the supporting pieces 111a, 111b, and 111c may include an actuator to control a bending angle. The user may adjust a range of a space between the bone 1 and the soft tissue 2 by adjusting the bending angles of the respective link connecting portions 112 using the controller 300.

Also, the supporting portion 111 may further include at least one flat light emitting device 117 at a bottom thereof. That is, the flat light emitting device 117 may be provided at the bottoms (toward the bone 1) of the respective supporting pieces 111a, 111b, and 111c constituting the supporting portion 111, thereby illuminating the inside of a locally open surgical area. The flat light emitting device may be formed of a light emitting diode (LED).

Meanwhile, the scratch forming unit 120 includes a driving portion 121 having a plurality of driving pieces 121a, 121b, and 121c which are link-connected and repeatedly moving based on one of the link connecting portions 122 to scratch the bone 1 and a scratching blade 125 provided at a free end of the driving portion 121 to scratch a fracture area of the bone 1 to form a callus.

Also, the driving portion 121 may further include at least one flat light emitting device 127 at a bottom thereof. That is, the flat light emitting devices 127 may be provided at the bottoms (toward the bone 1) of the respective supporting pieces 121a, 121b, and 121c constituting the driving portion 121, thereby illuminating the inside of the locally open surgical area. The flat light emitting device may be formed of an LED.

The link connecting portions 112 of the driving portion 121 of the scratch forming unit 120 may include actuators, respectively, to control bending angles.

Meanwhile, the driving portion 121 of the scratch forming unit 120 has the same shape of the supporting portion 111 of the surgical space providing unit 110 but performs an operation different therefrom. When the user drives the driving portion 121 while fixing one of the link connecting portions 122 of the driving portion 121 as a reference point using the controller 300, the driving portion 121 repeatedly moves and the scratching blade 125 provided at the free end of the driving portion 121 scratches the bone 1. This is performed like an operation of a woodpecker repeatedly pecking at a tree.

The scratching blade 125 may be formed to allow both sides of an end thereof to slant toward the center like an axe bit which is not like the peeling knife 115, which is preferable for efficiency of scratching the bone 1.

The manipulator 100 described above may be formed according to other embodiments.

Figure 9:
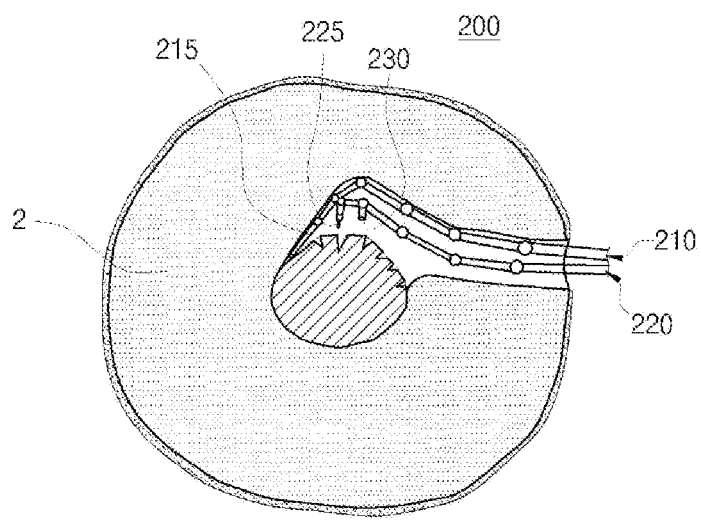
FIG. 9 is a side cross-sectional view illustrating a state in which a manipulator for fracture treatment performs surgery on a fracture area of the femur according to another embodiment of the present invention.
Figure 10:
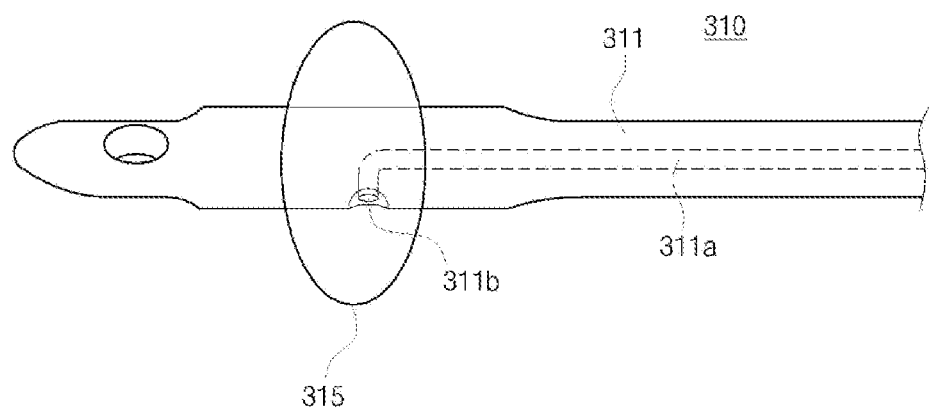
FIG. 10 is a perspective view of a surgical space providing unit according to still another embodiment of the present invention.
Figure 11:
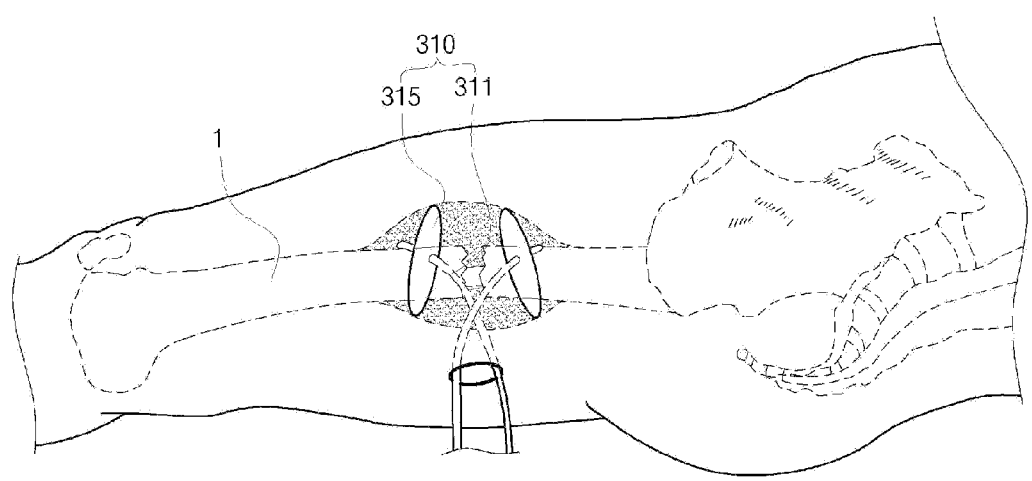
FIG. 11 is a schematic view of using the surgical space providing unit of FIG. 10.

FIG. 9 is a side cross-sectional view illustrating a state in which a manipulator 200 for fracture treatment performs surgery on a fracture area of the bone (femur) 1 according to another embodiment of the present invention. FIG. 10 is a perspective view of a surgical space providing unit 310 according to still another embodiment of the present invention. FIG. 11 is a schematic view of using the surgical space providing unit 310 of FIG. 10.

In the case of the manipulator 200 for fracture treatment according to another embodiment in FIG. 9, unlike the manipulator 100 for fracture treatment according to one embodiment of the present invention described above, an endoscope 230 is provided at a scratch forming unit 220.

In this case, since a surgical apparatus which invades a surgical area is simplified, it is possible to perform more locally invasive surgery. Also, the endoscope 230 is provided at the scratch forming unit 220 in FIG. 9 but may be provided at the surgical space providing unit 210.

In short, the endoscope 230 may be provided at the surgical space providing unit 210 or the scratch forming unit 220 and may minimize an invasive surgical area.

Meanwhile, unlike the manipulator 100 in accordance to one embodiment of the present invention, a manipulator 100 for fracture treatment of the present invention shown in FIGS. 10 and 11 has a structural difference in a surgical space providing unit 310 but has identical or equal structural features to the scratch forming unit 120 and the endoscope 130. Accordingly, a detailed drawing will be omitted.

The surgical space providing unit 310 shown in FIGS. 10 and 11 includes a supporting hose 311 and a supporting tube 315.

In detail, the supporting hose 311 includes a hollow portion 311a through which a gas or fluid flows and an outlet 311b formed at one side to be connected with the hollow portion 311a to discharge the gas or fluid which flows therein and may be formed of an elastic material.

The supporting tube 315 is provided at an outer circumferential surface of the supporting hose 311 while accommodating the outlet 311b of the supporting hose 311 and is filled with the gas or fluid discharged from the outlet 311b to increase in volume, thereby spacing the soft tissue 2 apart from the bone 1 and supporting the spaced soft tissue 2.

The surgical space providing unit 310 described above may be provided one but may be provided two as shown in FIG. 9 to spaciously support a surgical area.

Surgery using the locally invasive surgical apparatus including the manipulator for fracture treatment according to the embodiments of the present invention as described above may be performed as follows.

First, an incision is made to perform minimally invasive surgery on a fracture area which is delay-conglutinated and not conglutinated.

After that, the surgical space providing unit 110 or 210 is inserted into a fracture end, the peeling knife 115 or 215 of the surgical space providing unit 110 or 210 separates the bone 1 from the soft tissue 2, and the supporting portion 111 or 121 spaces and supports the separated soft tissue 2 apart from the bone 1.

After that, the scratch forming unit 120 or 220 is inserted into a spaced portion and scratches the fracture end to form a callus. Here, to provide a movement range of the scratch forming unit 120 or 220 driven to form a scratch, a height of the spaced portion may be controlled to be large by increasing bending angles of supporting pieces adjacent to the scratch forming unit 120 or 220.

In detail, referring to FIG. 4, the callus may be formed at the entire outer circumferential surface of the fracture end, the surgical space providing unit 110 may separate the bone 1 from the soft tissue 2 counterclockwise at about 180° at an invasive area, and the scratch forming unit 120 may form a scratch within this range. After that, the surgical space providing unit 110 peels the invasive area clockwise at about 180° at the invasive area, and then, the scratch forming unit 120 may scratch the peeled bone 1.

The locally invasive surgical apparatus according to the embodiments of the present invention which is able to perform minimally invasive surgery may perform fracture treatment which allows for less bleeding and quicker recovery.

As described above, it would be appreciated by those skilled in the art that various changes and modifications may be made without departing from the technical concept of the present invention and the technical scope of the present invention is not limited to the embodiments but is defined in the claims and their equivalents.

The invention claimed is:

1. A minimally invasive surgical apparatus comprising:
   a manipulator comprising,
      a surgical space providing unit formed from a plurality of first links and a peeling knife mounted to a free end of the plurality of first links,
      a scratch forming unit formed from a plurality of second links and a scratching blade mounted to a free end of the plurality of second links, and
      an endoscope;

a driving arm on which the manipulator is mounted; and
a controller for controlling the manipulator and the driving arm, wherein each of the plurality of the first links includes a first LED thereon and each of the plurality of the second links includes a second LED thereon.

2. The apparatus of claim 1, wherein a distal end of the peeling knife is angled with a first angle and a distal end of the scratching blade is angled with a second angle, and the first angle and the second angle are different one another.

3. The apparatus of claim 1, wherein the minimally invasive surgical apparatus further comprises a display unit which displays a part observed by the endoscope.

4. The apparatus of claim 3, wherein the endoscope is one of a two-dimensional (2D) endoscope and a three-dimensional (3D) endoscope.

5. The apparatus of claim 1, wherein the surgical space providing unit is configured to separate bone and soft fissile attached to each other.

6. The apparatus of claim 5, wherein each of the plurality of first links comprises a spacing link connecting portion and the spacing link connecting portion has an actuator to control a spacing bending angle.

7. The apparatus of claim 5, wherein the surgical space providing unit, the scratch forming unit, and the endoscope are arranged in an order.

8. The apparatus of claim 2, wherein the scratch forming unit is configured to scratch a bone by repeatedly moving the scratching blade with respect to one of the plurality of second links used as a reference point.

9. The apparatus of claim 8, wherein each of the plurality of second links comprises a driving link connecting portion and the driving link connecting portion has an actuator to control a driving bending angle.

10. The apparatus of claim 8, wherein the surgical space providing unit, the scratch forming unit, and the endoscope are arranged in an order.

11. The apparatus of claim 1, wherein a width of the peeling knife is wider than the scratching blade.

12. The apparatus of claim 1, wherein the surgical space providing unit, the scratch forming unit, and the endoscope are arranged in an order, and wherein a slant direction of the peeling knife of the surgical space providing unit is tilted toward the scratch forming unit.

* * * * *